(12) United States Patent
Honda et al.

(10) Patent No.: US 10,828,049 B2
(45) Date of Patent: Nov. 10, 2020

(54) MEDICAL DEVICE

(71) Applicant: TERUMO KABUSHIKI KAISHA, Tokyo (JP)

(72) Inventors: Kei Honda, Hadano (JP); Takehisa Mori, Hadano (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 152 days.

(21) Appl. No.: 15/073,759

(22) Filed: Mar. 18, 2016

(65) Prior Publication Data
US 2016/0270804 A1  Sep. 22, 2016

(30) Foreign Application Priority Data
Mar. 20, 2015 (JP) .................. 2015-058396

(51) Int. Cl.
*A61B 17/22* (2006.01)
*A61B 17/00* (2006.01)

(52) U.S. Cl.
CPC .... *A61B 17/22* (2013.01); *A61B 2017/00553* (2013.01); *A61B 2017/22079* (2013.01); *A61B 2217/005* (2013.01)

(58) Field of Classification Search
CPC ............. A61B 17/22; A61B 2217/005; A61B 2017/00553; A61B 2017/22079
See application file for complete search history.

(56) References Cited

U.S. PATENT DOCUMENTS

| | | | | |
|---|---|---|---|---|
| 6,176,848 B1* | 1/2001 | Rau | ...................... | F04D 29/0467 600/16 |
| 2003/0100816 A1* | 5/2003 | Siess | ..................... | A61M 1/101 600/16 |
| 2004/0210300 A1* | 10/2004 | Aboul-Hosn | ............ | A61F 2/07 623/1.23 |
| 2004/0215318 A1* | 10/2004 | Kwitkin | ................... | A61F 2/07 623/1.13 |
| 2006/0167539 A1* | 7/2006 | McEwan | .................. | A61F 2/01 623/1.35 |
| 2010/0185043 A1* | 7/2010 | Woodard | .............. | A61M 1/101 600/16 |
| 2016/0022890 A1* | 1/2016 | Schwammenthal | ...... | A61F 2/07 600/17 |

FOREIGN PATENT DOCUMENTS

JP 2001-512355 A 8/2001
WO WO 98/36694 A1 8/1998

* cited by examiner

*Primary Examiner* — Richard G Louis
(74) *Attorney, Agent, or Firm* — Buchanan Ingersoll & Rooney PC

(57) ABSTRACT

A medical device and method are disclosed which can cause a filter included in a cylinder to capture a capturing target by causing a fluid including a circulating flow to flow inside and around the cylinder introduced into a living body. The medical device has a filter, a cylinder, and an impeller. The filter captures a capturing target present inside a living body. The cylinder includes a lumen having the filter arranged therein, an aspiration section, which is open on the distal side of the lumen, and a discharge section which is open on a side surface on a proximal side of the lumen. The impeller is arranged on a proximal side of the filter in the lumen, and causes the lumen to aspirate the capturing target together with a fluid by causing the fluid to flow from the aspiration section toward the discharge section inside the living body.

20 Claims, 7 Drawing Sheets

MEDICAL DEVICE

CROSS-REFERENCES TO RELATED APPLICATIONS

This application claims priority to Japanese Patent Application No. 2015-058396 filed on Mar. 20, 2015, the entire content of which is incorporated herein by reference.

TECHNICAL FIELD

The present disclosure generally relates to a medical device.

BACKGROUND DISCUSSION

In the related art, treatments have been generally performed in which medical devices such as endoscopes and suction devices are introduced into a biological organ (for example, a body cavity such as an esophagus, airway, intestine, urinary duct, and other organs), and in which these devices are used so as to treat a lesion site appearing in the biological organ, or so as to perform removal of various foreign objects (capturing target) which are present inside the biological organ.

An example of the foreign object can include a calculus formed in the urinary tract. A urinary tract stone is the calculus, which is present in the urinary tract such as the kidney, urinary duct, bladder, and the urethra. In case of a urolithiasis, various symptoms can occur due to the urinary tract stone. For example, when the calculus formed inside the kidney moves to the urinary duct, the urinary duct can be injured by the calculus, thereby causing pain or hematuria. The calculus, for example, can occlude the urinary duct, thereby bringing a patient into a transient hydronephrosis state. Consequently, the patient may feel a severe pain (colicky pain) in a range from the waist back to the flank. The removal of the calculus can be an effective means for relieving or treating the symptoms.

In order to remove the calculus, a method has been widely used in which the calculus is picked and extracted by using basket forceps (refer to JP-T-2001-512355). However, it can be necessary to pick the calculus one by one and to extract the calculus from a living body. Consequently, the method is a very laborious task.

Here, for example, a method is conceivable in which a filter for use in removing a foreign object inside the blood vessel can be diverted for the purpose of efficiently extracting the calculus, and which collectively captures the calculus aspirated together with a fluid by causing the fluid including a circulating flow to flow inside and around a cylinder having the filter arranged therein.

However, since the cylinder is introduced into a living body, it can be necessary to reduce a size of the cylinder as much as possible. Moreover, if it is considered that more capturing targets have to be accommodated inside the cylinder, it is not practical to increase a size of a structure for causing the circulating flow to flow and to obtain a sufficient suction force. Therefore, it is not easy to cause the filter included in the cylinder to sufficiently capture the capturing target.

SUMMARY

A medical device is disclosed, which can cause a filter included in a cylinder to sufficiently capture a capturing target by causing a fluid including a circulating flow to flow inside and around the cylinder introduced into a living body.

A medical device is disclosed according to the present disclosure, which includes a filter for capturing a capturing target present inside a living body, a cylinder that includes a lumen having the filter arranged therein, an aspiration section which is open on a distal side of the lumen, and a discharge section which is open on a side surface on a proximal side of the lumen, and an impeller that is arranged on the further proximal side from the filter in the lumen, and that causes the lumen to aspirate the capturing target together with a fluid by causing the fluid to flow from the aspiration section toward the discharge section inside the living body. At least a portion on the proximal side of the impeller is arranged at a position facing the discharge section in a region inside the lumen.

According to a medical device, between an aspiration section on a distal side of a lumen and a discharge section on a side surface on a proximal side of the lumen, an impeller in which at least a portion on the proximal side is arranged at a position facing the discharge section in a region inside the lumen causes a fluid including a circulating flow configured to partially have a flow inside the lumen from the aspiration section toward the discharge section to flow in the lumen and around a cylinder. According to this configuration, the medical device can cause the discharge section to efficiently discharge the fluid which is aspirated from the aspiration section and which moves radially outward due to centrifugal force generated by the rotation of the impeller, and can cause the aspiration section to circulate the fluid.

Accordingly, the medical device can obtain a sufficient suction force without attenuating the flow of the fluid including the circulating flow caused to flow inside and around the cylinder. Therefore, the medical device can sufficiently aspirate and capture a capturing target.

A method is disclosed for capturing a target present inside a living body, the method comprising: inserting a medical device comprising a filter for capturing a capturing target, a cylinder that includes a lumen having the filter arranged therein, an aspiration section which is open on a distal side of the lumen, a discharge section which is open on a side surface on a proximal side of the lumen, and an impeller that is arranged on a proximal side from the filter in the lumen, wherein at least a portion on a proximal side of the impeller is arranged at a position facing the discharge section in a region inside the lumen; and aspirating the capturing target with the lumen and a fluid by flowing the fluid from the aspiration section toward the discharge section inside the living body.

BRIEF DESCRIPTION OF THE DRAWINGS

FIGS. 6(A)-6(C) are side views schematically illustrating a state where a capturing target is collected in the accommodation unit of the medical device illustrated in FIG. 1, wherein FIG. 6(A) is a view illustrating a state before the capturing target is collected in the accommodation unit, FIG. 6(B) is a view illustrating a state while the capturing target is collected in the accommodation unit, and FIG. 6(C) is a view illustrating a state after the capturing target is collected in the accommodation unit.

FIGS. 9(A) and 9(B) are views illustrating an accommodation unit of a medical device according to Modification Example 2 (first example) of the embodiment, wherein FIG. 9(A) is a view illustrating a cylinder and an impeller by using a cross section viewed from a side along the axial direction, and FIG. 9(B) is a view illustrating the impeller viewed from the distal side toward the proximal side along the axial direction.

FIGS. 10(A) and 10(B) are views illustrating the accommodation unit of the medical device according to Modification Example 2 (second example) of the embodiment, wherein FIG. 10(A) is a view illustrating the cylinder and an impeller by using a cross section viewed from a side along the axial direction, and FIG. 10(B) is a view illustrating the impeller viewed from the distal side toward the proximal side along the axial direction.

FIGS. 11(A) and 11(B) are views illustrating the accommodation unit of the medical device according to Modification Example 2 (third example) of the embodiment, wherein FIG. 11(A) is a view illustrating the cylinder and an impeller by using a cross section viewed from a side along the axial direction, and FIG. 11(B) is a view illustrating the impeller viewed from the distal side toward the proximal side along the axial direction.

FIGS. 12(A) and 12(B) are views illustrating an accommodation unit of a medical device according to Modification Example 3 of the embodiment, wherein FIG. 12(A) is a view illustrating a cylinder and an impeller by using a cross section viewed from a side along the axial direction, and FIG. 12(B) is a view illustrating the impeller viewed from the distal side toward the proximal side along the axial direction.

DETAILED DESCRIPTION

Figure 1:
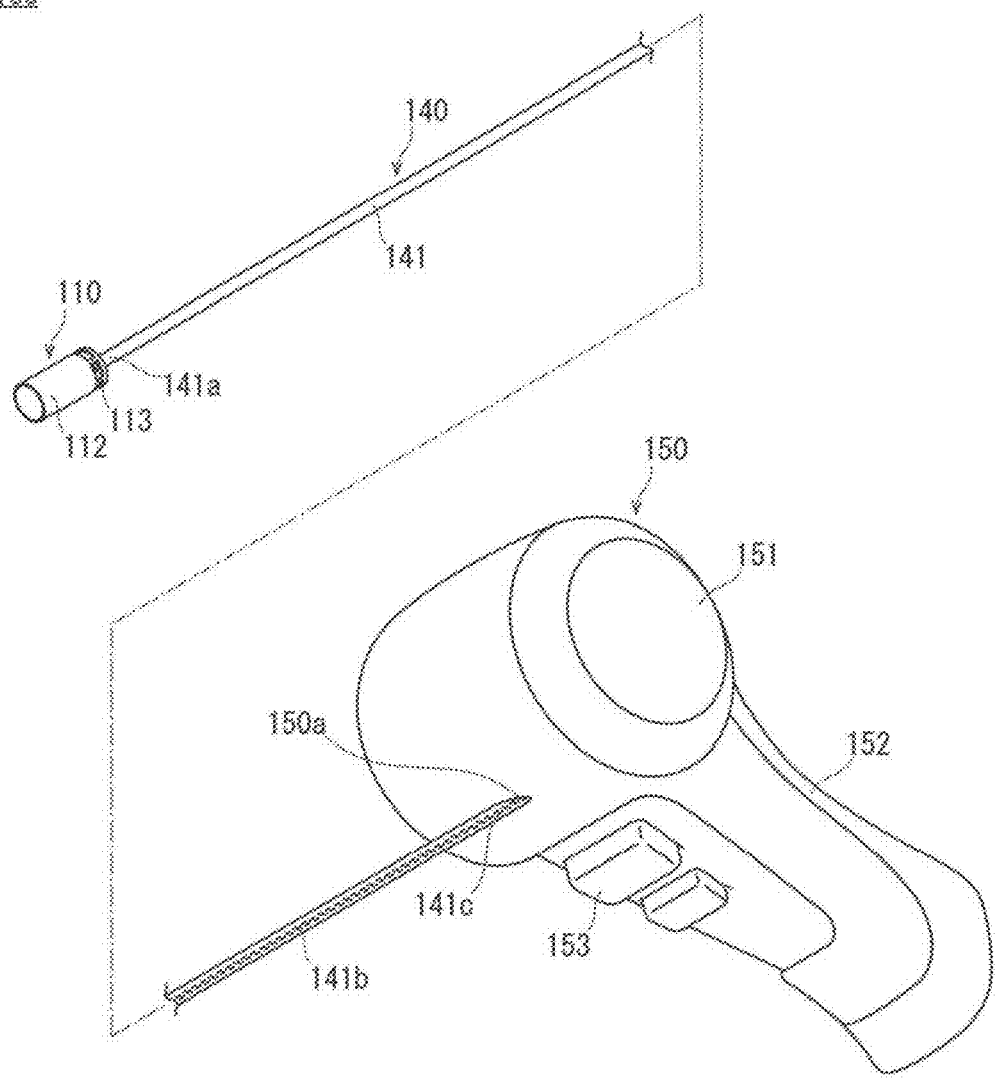
FIG. 1 is a perspective view illustrating a medical device according to an embodiment.

Hereinafter, embodiments of the present disclosure will be described with reference to the drawings. In some cases, dimensional proportions in the drawings may be exaggerated and different from actual proportions for convenience of description. In a medical device 100, an accommodation unit 110 side which is introduced into a living body corresponds to a distal side, and a hand operation unit 150 operated by a user (operator) corresponds to a proximal side.

The medical device 100 according to an embodiment will be described with reference to FIGS. 1 to 6(C).

A configuration of the medical device 100 will be described with reference to FIGS. 1 to 3.

According to the medical device 100, a cylinder 112 introduced into a living body (for example, a urinary duct 630) causes a fluid including a circulating flow G configured to partially have a flow of the fluid inside a lumen 112b from an aspiration section 112a toward a discharge section 112c to flow in the lumen 112b and around the cylinder 112, and a filter 111 included in the cylinder 112 sufficiently captures a capturing target (for example, a solid calculus K or a semi-solid blood clot). As for the capturing target, the calculus K can include calculus fragments obtained by fragmenting the calculus K present in the urinary duct 630 by using a laser lithotripsy device, for example, and by relatively decreasing a size thereof. The accommodation unit 110, an introduction unit 140, and a hand operation unit 150 which configure the medical device 100 will be sequentially described.

Figure 2:
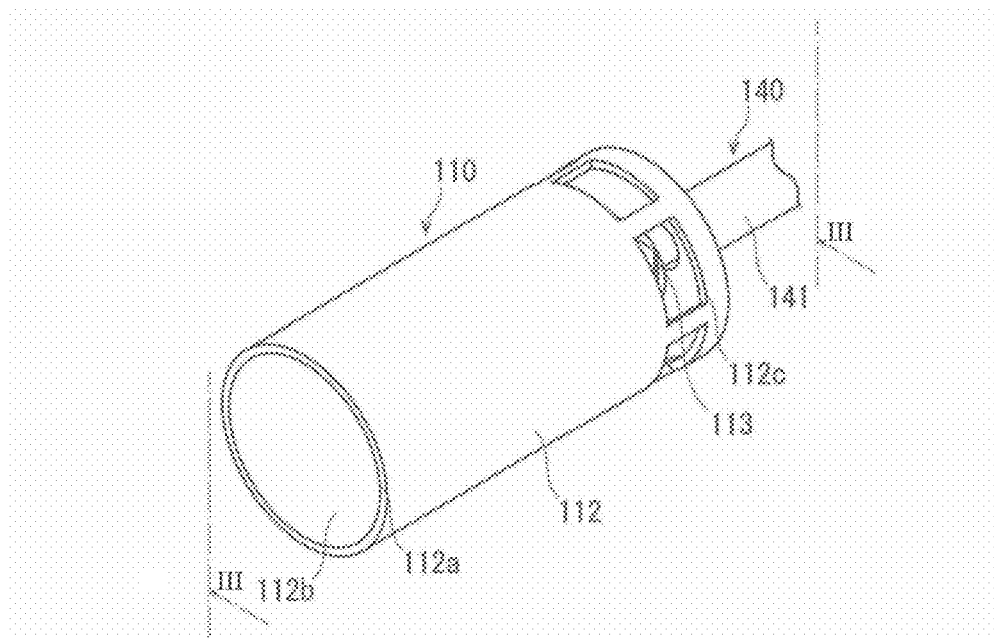
FIG. 2 is a perspective view illustrating an accommodation unit in the medical device in FIG. 1.
Figure 3:
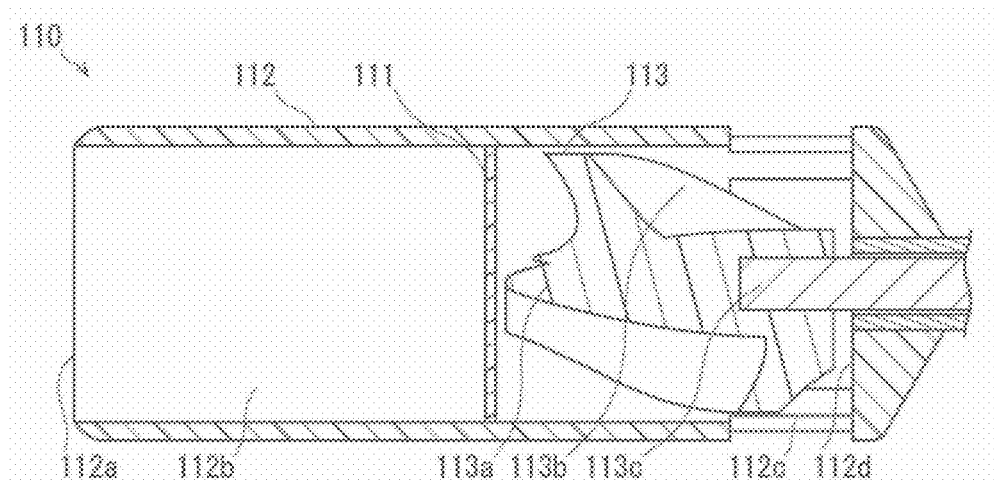
FIG. 3 is a side view illustrating the accommodation unit in the medical device in FIG. 1 by using a cross section taken along line III-III in FIG. 2.

As illustrated in FIGS. 1 to 3, the accommodation unit 110 accommodates the capturing target which is present inside the living body such as the urinary duct 630.

The accommodation unit 110 can include the filter 111, the cylinder 112, and an impeller 113.

The filter 111 captures the capturing target present inside the living body.

The filter 111 adopts a configuration which allows a fluid to pass therethrough and does not allow the capturing target including a solid calculus K or a semi-solid blood clot to pass therethrough, for example. That is, the filter 111 can distinguish the capturing target from the fluid, and can capture the capturing target moved together with the fluid from the aspiration section 112a toward the discharge section 112c of the cylinder 112. The filter 111 is joined to the further distal side from the impeller 113 in the lumen 112b of the cylinder 112. The filter 111 can include a holding unit, which is formed in a lattice shape and which holds the capturing target, and a frame portion, which is formed in a ring shape and which is integrally formed in an outer peripheral edge of the holding unit.

For example, the filter 111 can be configured by using a woven fabric formed of woven stuff or knitted fabric, a fibrous material formed of mesh fabric having a predetermined mesh such as non-woven fabric, or a porous film. In particular, for example, the mesh fabric can have a relatively uniform mesh. Accordingly, the mesh fabric can suitably configure the filter 111. The filter 111 may be configured to include a combination of the above-described multiple materials.

The cylinder 112 accommodates the capturing target captured by the filter 111.

The cylinder 112 can include the lumen 112b having the filter 111 arranged therein, the aspiration section 112a which is open on the distal side of the lumen 112b, and the discharge section 112c which is open on a side surface on the proximal side of the lumen 112b.

The cylinder 112 is formed in a cylindrical shape. The cylinder 112 is formed so that the thickness is thinner compared to the diameter, and is formed so that the length along the axial direction is longer compared to the diameter. The cylinder 112 has the lumen 112b formed in order to accommodate the capturing target inside of the cylinder 112.

The aspiration section 112a is open on the distal side of the lumen 112b, and functions as an opening for aspirating the capturing target together with the fluid. The aspiration section 112a is formed in a circular shape in a cross section orthogonal to the axis.

The discharge section 112c is open on a side surface on the proximal side of the lumen 112b, and functions as an opening for discharging the fluid passing through the filter 111 into the living body (for example, the urinary duct 630 into which the cylinder 112 is introduced). A shape or the number of discharge sections 112c, and an arrangement between the discharge sections 112c are not particularly limited. For example, a configuration having one large discharge section 112c, or a configuration having many small discharge sections 112c may be adopted. In addition, a configuration may be adopted in which the shape of the discharge section 112c is formed in a shape whose opening area gradually increases from the distal side to the proximal side, and in which the fluid discharged from the discharge section 112c is also likely to be discharged toward the proximal side. For example, as described in the present embodiment, a configuration may be adopted in which each discharge section 112c is formed in a rectangular shape along the radial direction, and in which the discharge section 112 is open at multiple locations at a constant interval along the circumferential direction on the proximal side of the cylinder 112. According to this configuration, the fluid is discharged from each discharge section 112c, thereby allowing a uniform flow of the fluid in the circumferential direction of the cylinder 112.

The lumen 112b of the cylinder 112 can include the impeller 113 so as to be rotatable. The cylinder 112 has a support hole which supports an axle portion 113c of the impeller 113 by being rotatably inserted into a proximal portion 112d on the most proximal side. The support hole can include an opening penetrating along the axial direction, at a central portion of the proximal portion 112d.

The filter 111 is joined to the lumen 112b of the cylinder 112 at a position on the further distal side from the impeller 113. The capturing target is accommodated in a region from the position of the aspiration section 112a on the distal side to the position to which the filter 111 is joined, in the lumen 112b.

For example, the cylinder 112 can be configured to include a rigid material formed of polyolefin, such as acrylic resin, polyvinyl chloride (particularly, rigid polyvinyl chloride), polyethylene, polypropylene, or polybutadiene. The cylinder 112 is configured to include a material which is transparent in a visible light region, and can be configured so that capturing progress of the capturing target is visible from the outside. For example, the cylinder 112 can be configured to include an X-ray contrast agent. The contrast agent is imaged from the outside by using X-ray fluoroscopy. In this manner, a position of the cylinder 112 inside the living body can be confirmed.

The impeller 113 causes the lumen 112b of the cylinder 112 to aspirate the capturing target together with the fluid by using a generated flow of the fluid including the circulating flow G.

The impeller 113 is arranged on the further proximal side from the filter 111 in the lumen 112b, and causes the lumen 112b to aspirate the capturing target by causing the fluid to flow from the aspiration section 112a toward the discharge section 112c inside the living body.

At least a portion on the proximal side of the impeller 113 is arranged at a position facing the discharge section 112c in a region inside the lumen 112b. That is, at least a portion on the proximal side of the impeller 113 is arranged so as to be located between the distal end and the proximal end of the discharge section 112c along the axial direction of the cylinder 112. Therefore, the impeller 113 can smoothly discharge the fluid, which moves radially outward due to centrifugal force from the discharge section 112c located on a side surface of the cylinder 112.

The impeller 113 is rotatably accommodated inside the cylinder 112. The impeller 113 can include a shaft portion 113a, multiple blade portions 113b, and the axle portion 113c. For example, the impeller 113 configures a propeller-type screw as a whole by using the shaft portion 113a and the multiple blade portions 113b. The impeller 113 may be configured to function as a screw of a paddle type, a turbine type, or a ribbon type.

Along the axial direction, the shaft portion 113a rotates the blade portion 113b which is joined at multiple locations at a constant interval along the circumferential direction. The shaft portion 113a is a columnar body whose diameter on the distal side (upstream side along the axial direction) is reduced, and has a bullet shape as a whole. The elongated and elastic axle portion 113c is interlocked with an end portion on the proximal side (downstream side along the axial direction) of the blade portion 113b. The axle portion 113c is connected to a motor of a control member 151 of the hand operation unit 150.

The blade portion 113b corresponds to a screw blade portion. If the blade portion 113b is rotated by the shaft portion 113a, a fluid is caused to flow from the aspiration section 112a toward the discharge section 112c of the cylinder 112. That is, while the blade portion 113b is rotated, the fluid is caused to flow from the aspiration section 112a toward the discharge section 112c of the cylinder 112.

In the blade portion 113b, the length along the axial direction is longer than the length along the radial direction. The blade portion 113b is longitudinally twisted from the distal side to the proximal side based on a rotation axis so that the rotation of the shaft portion 113a enables a fluid to flow. Furthermore, the blade portion 113b is bent radially outward from the rotation axis in a direction opposite to the rotation direction.

Incidentally, the impeller 113 is configured so that the shaft portion 113a is formed in a bullet shape as a whole, or so that the blade portion 113b is formed to be longitudinally twisted from the distal side to the proximal side based on a rotation axis. If this impeller 113 is used, in the fluid caused to flow by the rotation of the blade portion 113b, a flow (vector) in the horizontal direction with respect to the radial direction and a flow (vector) in the vertical direction from the proximal side toward the distal side are mixed with each other. In this case, a flow of the fluid is formed as if the fluid swirls down in a direction toward the distal end from the proximal side surface of the impeller 113. Here, according to the impeller 113 in the present embodiment, at least a portion on the proximal side is arranged so as to be located between the distal end and the proximal end of the discharge section 112c along the axial direction of the cylinder 112. Accordingly, the flow of the fluid from the impeller 113 toward the discharge section 112c may not be disturbed in a region of the discharge section 112c. Therefore, even when the flow of the fluid is formed as if the fluid swirls down in the direction to the distal end from the proximal side surface of the impeller 113, the fluid from the discharge section 112c located on a side surface of the cylinder 112 can be smoothly discharged.

Except for the axle portion 113c, for example, the impeller 113 can be configured to include a rigid resin material formed of polyolefin, such as acrylic resin, polyvinyl chloride (particularly, rigid polyvinyl chloride), polyethylene, polypropylene, or polybutadiene. In addition, except for the axle portion 113c, for example, the impeller 113 can be configured to include a metal material, which is a pseudo-elastic alloy (including a super-elastic alloy) such as a Ni—Ti alloy, a shape memory alloy, stainless steel, a cobaltbased alloy, precious metal such as gold and platinum, a tungsten-based alloy, or a carbon-based material (including a piano wire). The axle portion 113c can be configured to include a flexible material.

As illustrated in FIGS. 1 to 3, the introduction unit 140 is used by an operator in order to introduce the accommodation unit 110 into the living body such as the urinary duct 630.

The introduction unit 140 can include an introduction tube 141. The introduction tube 141 is formed in an elongated cylinder shape. A lumen 141b which can rotatably hold the axle portion 113c of the impeller 113 is formed inside the introduction tube 141. A distal end 141a of the introduction tube 141 is joined to the support hole which is open in the proximal portion 112d of the cylinder 112. A proximal end 141c of the introduction tube 141 is connected to a connection port 150a of the hand operation unit 150 so as to be attachable and detachable. The introduction tube 141 is configured to include a flexible material, and can be deformed in accordance with the shape of, for example, the urinary duct 630, or the movement of the flexible scope 700.

As illustrated in FIG. 1, the hand operation unit 150 is operated by an operator in order to adjust a position of the cylinder 112 introduced into the urinary duct 630, or in order to rotate the impeller 113.

The hand operation unit 150 can include the control member 151, a gripping member 152, and a switch 153. The hand operation unit 150 can include a connection port 150a for connecting the proximal end 141c of the introduction tube 141 of the introduction unit 140 so as to be attachable and detachable. The control member 151 can include a motor for rotating the axle portion 113c of the impeller 113, a control circuit for controlling the motor, and a power source (battery) for supplying power to the motor and the control circuit. A rotary shaft of the motor is interlocked with the axle portion 113c of the impeller 113 so as to be attachable and detachable. If the motor of the control member 151 is rotated, the axle portion 113c of the impeller 113 introduced into the introduction tube 141 is rotatably driven, thereby rotating the impeller 113 inside the cylinder 112. The gripping member 152 is gripped by an operator. The gripping member 152 internally stores a battery of the control member 151. The switch 153 turns on and off the motor of the control member 151.

A method of using the medical device 100 will be described with reference to FIGS. 4 to 6(C).

Figure 5:
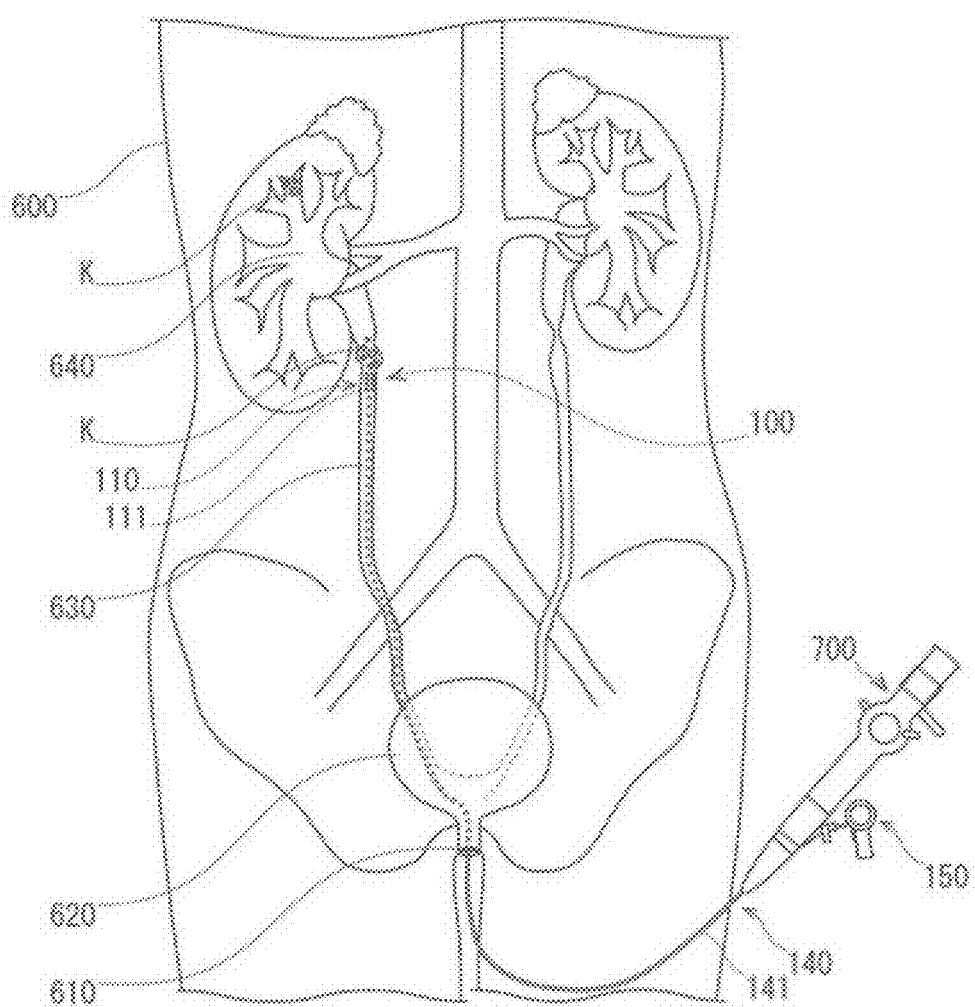
FIG. 5 is a view schematically illustrating a state where the flexible scope on which the medical device illustrated in FIG. 1 is mounted is introduced into a patient's urinary duct.

Hereinafter, a patient 600 who suffers from the urolithiasis will be described by citing a treatment example where the patient 600 has a calculus K present in a region corresponding to a lower urinary duct of the urinary duct 630 which is reachable by a rigid scope, and also has a calculus K in a region corresponding to an upper urinary duct of the urinary duct 630 which is less likely to be reachable by the rigid scope but is reachable by the flexible scope. In this case of disease, the calculus K in the lower urinary duct is first removed, and then the calculus K in the upper urinary duct is removed. FIG. 5 schematically illustrates a situation when the calculus K in the upper urinary duct is removed after the calculus K in the lower urinary duct is removed.

In the description relating to the method of using the medical device 100, the capturing target will be described as the calculus K, for example.

In order to treat the patient 600 illustrated in FIG. 5, a cystoscope generally used in the urinary system is used so as to introduce a guidewire widely known in the medical field into the urinary duct 630 or a renal pelvis and renal calyx 640 via a urethra 610 and a bladder 620. Next, a rigid pyeloscope (hereinafter, referred to as a rigid scope) is inserted so as to observe an inner wall of the urinary duct 630 or the calculus K inside the urinary duct 630. In this case, the calculus K may be removed by using the rigid scope in combination with basket forceps. In addition, the rigid scope may be used in combination with a fragmenting device, such as, for example, a holmium YAG laser so as to fragment the relatively large calculus K which is less likely to be removed into smaller fragments. Alternatively, the generated calculus fragments may be removed by using the basket forceps. Thereafter, the rigid scope is removed from the inside of the living body.

Next, a ureteral access sheath is introduced into the urinary duct 630 or the renal pelvis and renal calyx 640 via the urethra 610 and the bladder 620 through the guidewire.

The flexible scope 700 is inserted via the ureteral access sheath so as to observe the calculus K. In this case, the guidewire may be removed. When the calculus K has a relatively large size which is less likely to pass through the ureteral access sheath, the flexible scope 700 can be used in combination with the fragmenting device such as, for example, the holmium YAG laser so as to fragment the calculus K into a relatively small size.

Figure 4:
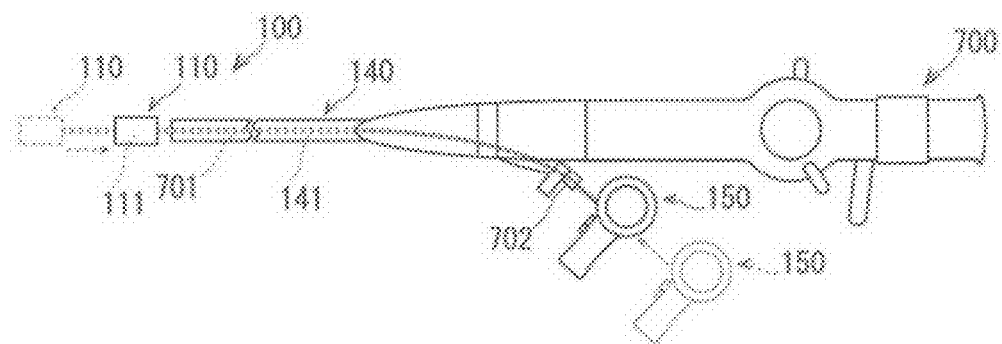
FIG. 4 is a side view schematically illustrating a state where the medical device illustrated in FIG. 1 is mounted on a flexible pyeloscope (hereinafter, referred to as a flexible scope).

Next, the medical device 100 and the flexible scope 700 are assembled to each other. Specifically, as illustrated in FIG. 4, in a state where the introduction tube 141 and the hand operation unit 150 in the medical device 100 are separated from each other, the introduction tube 141 is introduced into a working channel 701 of the flexible scope 700 from the distal side of the flexible scope 700. The proximal side of the introduction tube 141 is extracted from a port 702, and the proximal side of the introduction tube 141 is fitted and attached to the hand operation unit 150.

Next, as illustrated in FIG. 5, the flexible scope 700 having the medical device 100 mounted thereon passes through the urethra 610 and the bladder 620 of the patient 600 via the ureteral access sheath, and reaches a site having the calculus K present inside the urinary duct 630, for example. Thereafter, the calculus K is collected in the accommodation unit 110 by using the medical device 100.

Figure 6A:
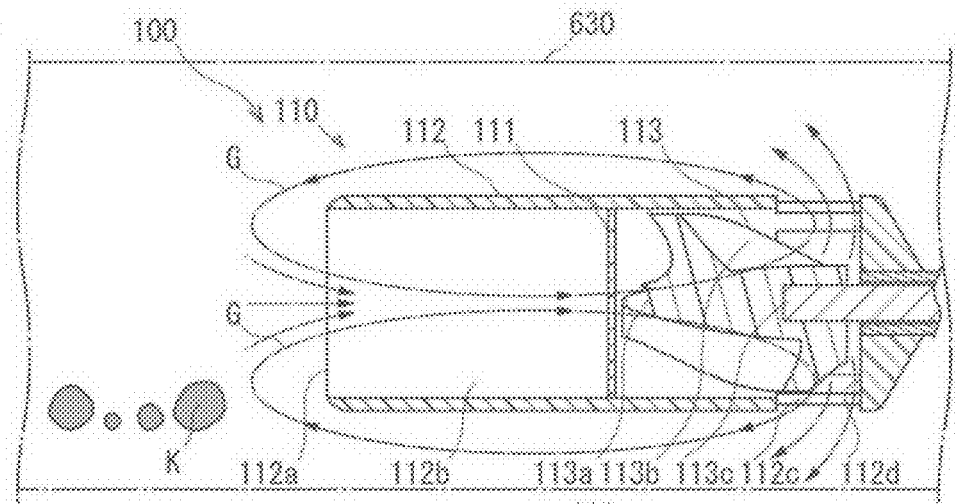
Figure 6B:
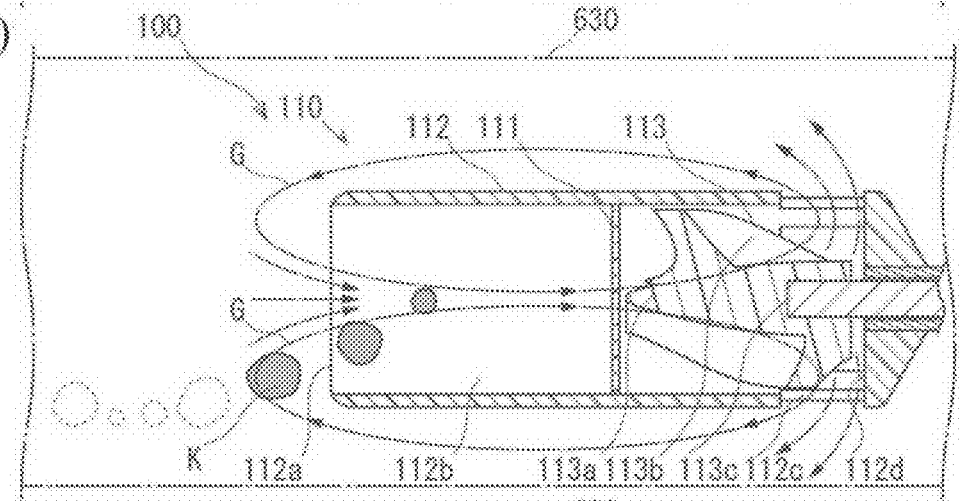
Figure 6C:
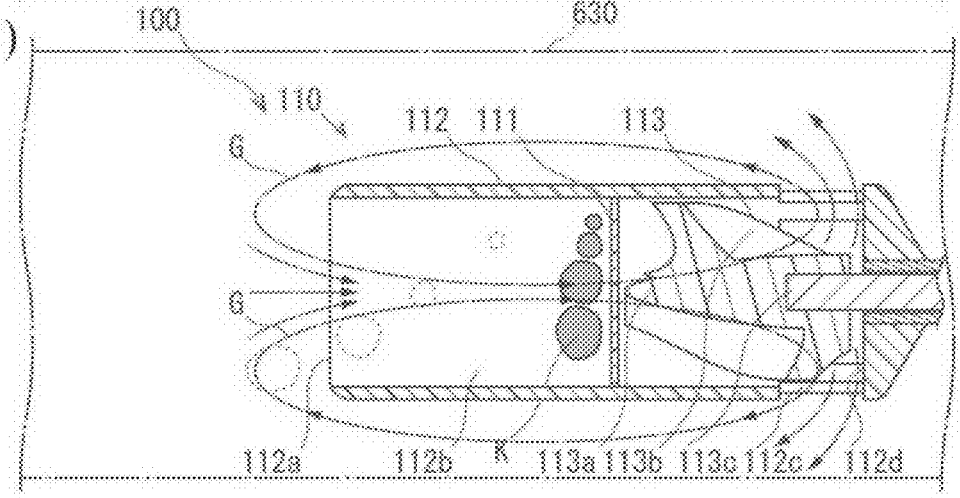

Specifically, for example, as illustrated in FIG. 6(A), the cylinder 112 is moved close to the calculus K inside the urinary duct 630 illustrated in FIG. 5. If an operator operates the switch 153 of the hand operation unit 150 so as to rotate the impeller 113, a flow of a fluid is generated, including the circulating flow G, which flows from the aspiration section 112a which is open on the distal side of the cylinder 112 toward the discharge section 112c which is open on the side surface on the proximal side, and further flows toward the aspiration section 112a after being discharged from the discharge section 112c and is aspirated from the aspiration section 112a and discharged from the discharge section 112c. As a result, a strong suction force acting from the aspiration section 112a toward the discharge section 112c is generated around the aspiration section 112a and inside the cylinder 112. As illustrated in FIGS. 6(B) to 6(C), the calculus K inside the urinary duct 630 is moved and captured while being attracted to the filter 111 arranged in the cylinder 112. The calculus K captured by the filter 111 is accommodated in the cylinder 112. Next, the cylinder 112, which collects the calculus K in the cylinder 112, is conveyed outward from the body in a state where the suction force is generated. The calculus K inside the cylinder 112 can then be removed outside the body.

Then, the accommodation unit 110 of the medical device 100 is caused to reach the site having the calculus K again. Thereafter, the calculus K is repeatedly aspirated into the cylinder 112, and is repeatedly removed outside the body.

Furthermore, in order to change a position of (reposition) the calculus K, the medical device 100 may be controlled so that the calculus K is aspirated into the cylinder 112 in a renal calyx located inside the renal pelvis and renal calyx, and so that the rotation of the motor is minimized or stopped in the other renal calyx. In this manner, the calculus K may be released from the cylinder 112. In this case, an operation may be performed so as to discharge the calculus K from the cylinder 112 by reversely rotating the motor.

The medical device 100 may be used together with the rigid scope. That is, instead of the basket forceps, the rigid scope may be used for observing, fragmenting, and extracting operations which are performed before the extracting operation is performed by using the flexible scope 700.

Next, the guidewire is introduced into the urinary duct 630 or the renal pelvis and renal calyx 640 via the urethra 610 and the bladder 620. This operation may be performed via the ureteral access sheath. Furthermore, a ureteral stent for upper urinary duct indwelling is caused to indwell while covering the guide wire, and thereafter the guidewire is removed. The ureteral stent corresponds to a transient ureteral obstruction after operation. After a predetermined number of days elapses, the ureteral stent is removed.

Whether to use the ureteral access sheath or not is determined by an operator in view of conditions, for example, of the urinary duct, or the calculus K. That is, without using the ureteral access sheath, observing, fragmenting, and extracting operations may be performed by using the flexible scope 700. Even in this case, the medical device 100 may be used together with the flexible scope 700.

As described above, according to the medical device 100 of the embodiment, the following configurations provide an operation effect.

According to the medical device 100, between the aspiration section 112a on the distal side of the lumen 112b and the discharge section 112c on the side surface on the proximal side of the lumen 112b, the impeller 113 in which at least a portion on the proximal side is arranged at a position facing the discharge section 112c in a region inside the lumen 112b causes a fluid including the circulating flow G configured to partially have a flow inside the lumen 112b from the aspiration section 112a toward the discharge section 112c to flow in the lumen 112b and around the cylinder 112. According to this configuration, the medical device 100 can cause the discharge section 112c to efficiently discharge the fluid, which is aspirated from the aspiration section 112a, and which moves radially outward due to centrifugal force generated by the rotation of the impeller 113, and can cause the aspiration section 112a to circulate the fluid. Accordingly, the medical device 100 can obtain a sufficient suction force without attenuating the flow of the fluid including the circulating flow G caused to flow inside and around the cylinder. Therefore, the medical device 100 can sufficiently aspirate and capture the capturing target.

A medical device according to Modification Example 1 of the embodiment will be described with reference to FIGS. 7 and 8. In the medical device according to Modification Example 1 of the embodiment, a configuration in which the proximal portion of the cylinder is bent into a concave shape is different from the configuration of the medical device 100 according to the above-described embodiment. In the medical device 100 according to the embodiment, the proximal portion 112d of the cylinder 112 is configured to have a planar shape. In Modification Example 1 according to the embodiment, the same reference numerals are given to the same configuration elements as those in the embodiment, and repeated description will be omitted.

A configuration of an accommodation unit 210 according to Modification Example 1 (first example and second example) of the embodiment will be described with reference to FIGS. 7 and 8.

Figure 7:
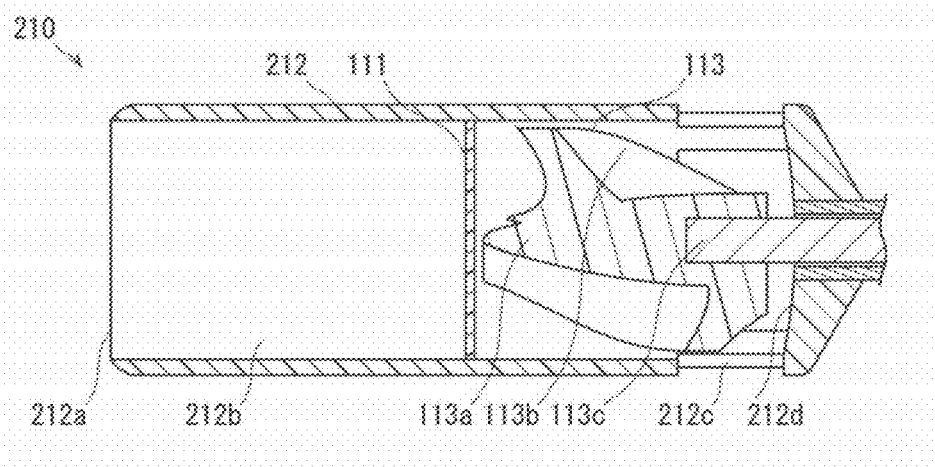
FIG. 7 is a side view illustrating a cylinder and an impeller of an accommodation unit in a medical device according to Modification Example 1 (first example) of the embodiment, by using a cross section viewed from a side along the axial direction.

FIG. 7 is a side view illustrating a cylinder 212 and the impeller 113 of the accommodation unit 210 in a medical device according to Modification Example 1 (first example) of the embodiment, by using a cross section viewed from a side along the axial direction. FIG. 8 is a side view illustrating the cylinder 214 and the impeller 113 of the accommodation unit 210 in the medical device according to Modification Example 1 (second example) of the embodiment, by using a cross section viewed from a side along the axial direction.

In the medical device, as illustrated in FIG. 7, the cylinder 212 is formed so that a proximal portion 212d which is further separated toward the proximal side from an aspiration section 212a than a discharge section 212c is bent into a concave shape. The proximal portion 212d is formed in a concave bowl shape, which is continuously changed so as to greatly tilt toward the distal side as the shape extends radially outward from the central axis of the cylinder 212. The proximal portion 212d of the cylinder 212 is located on the further proximal side along the axial direction from the blade portion 113b of the impeller 113.

Figure 8:
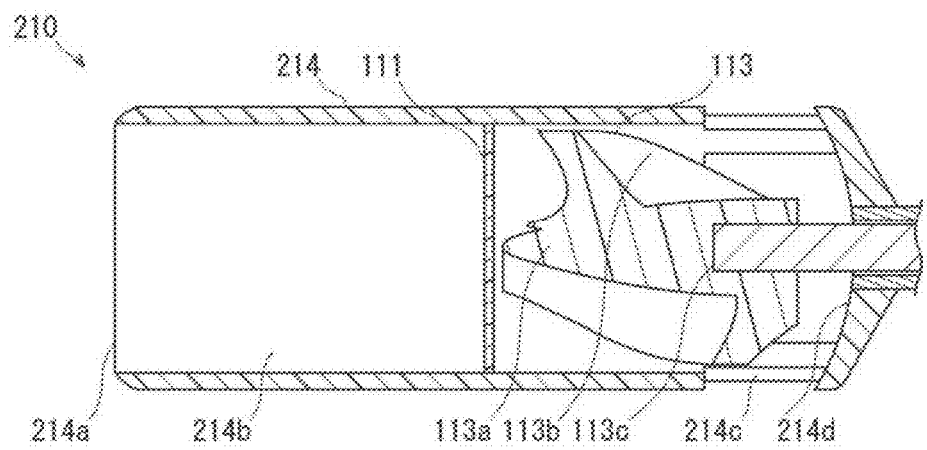
FIG. 8 is a side view illustrating the cylinder and the impeller of the accommodation unit in the medical device according to Modification Example 1 (second example) of the embodiment, by using a cross section viewed from a side along the axial direction.

In the medical device, as illustrated in FIG. 8, the cylinder 214 is formed so that a proximal portion 214d is continuously bent including a discharge section 214c. According to this configuration, the fluid which is aspirated from an aspiration section 214a and which flows toward the proximal portion 214d after passing through the impeller 113 is discharged into the living body via the discharge section 214c which is integrally formed in a concave shape continuous with the proximal portion 214d.

As described above, according to the medical device in Modification Example 1 of the embodiment, the following configurations provide an operation effect.

In the medical device, the cylinder 212 is formed so that the proximal portion 212d which is further separated to the proximal side from the aspiration section 212a than the discharge section 212c is bent into a concave shape. According to the medical device having this configuration, the fluid which is aspirated from the aspiration section 212a and which flows toward the proximal portion 212d after passing through the impeller 113 can be propagated so as to rebound in a direction toward the aspiration section 212a through the lateral side of the lumen 212b and the discharge section 212c while pressure loss is suppressed, by the proximal portion 212d bent into a concave shape. Therefore, the medical device can relatively quickly discharge the fluid propagated in the direction toward the aspiration section 212a through the lateral side of the lumen 212b and the discharge section 212c, from the discharge section 212c included on the side surface of the lumen 212b. The medical device can guide the fluid to flow toward the aspiration section 212a side of the cylinder 212 after passing a portion between the living body and the cylinder 212. That is, the proximal portion 212d formed in a concave shape helps enable the circulating flow between the aspiration section 212a and the discharge section 212c to be relatively smooth. Therefore, the medical device can efficiently aspirate and capture the capturing target.

Furthermore, in the medical device, the proximal portion 214d is formed so as to be continuously bent including the discharge section 214c. According to the medical device having this configuration, a flow of the fluid propagated in the direction toward the aspiration section 212a through the lateral side of the lumen 214b and the discharge section 212c can be quickly discharged into the living body from the proximal portion 214d via the discharge section 214c without being disturbed in a region of the discharge section 214c. That is, the proximal portion 214d formed in a concave shape including the discharge section 214c helps enable the circulating flow between the aspiration section 214a and the discharge section 214c to be relatively smooth. Therefore, the medical device can more efficiently aspirate and capture the capturing target.

A medical device according to Modification Example 2 of the embodiment will be described with reference to FIGS. 9 to 11. In the medical device according to Modification Example 2 of the embodiment, the inner diameter of the cylinder, the number of blade portions in the impeller, and a configuration in which the radius of curvature of the blade portion is defined in a specific range are different from the configurations of the medical device 100 according to the above-described embodiment. In Modification Example 2 according to the embodiment, the same reference numerals are given to the same configuration elements as those in the embodiment, and repeated description will be omitted.

A configuration of an accommodation unit 310 according to Modification Example 2 (first example to third example) of the embodiment will be described with reference to FIGS. 9(A) to 11(B).

Figure 9A:
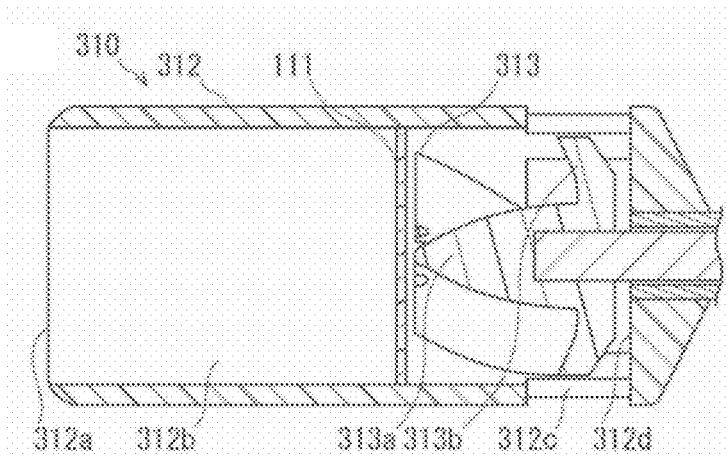
Figure 9B:
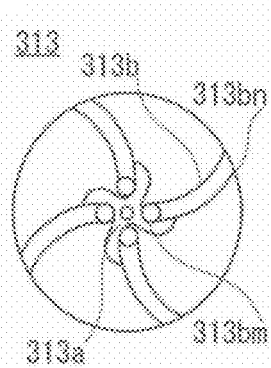
Figure 10A:
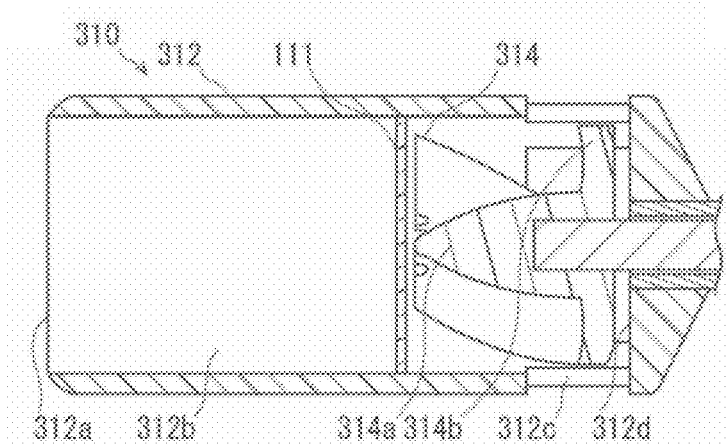
Figure 10B:
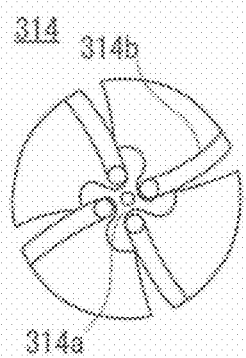
Figure 11A:
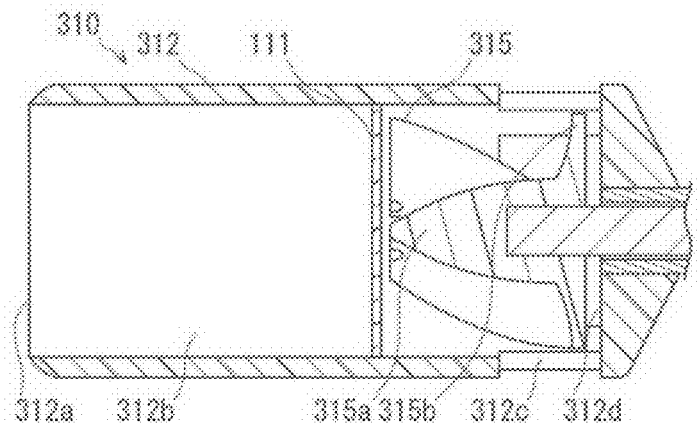
Figure 11B:
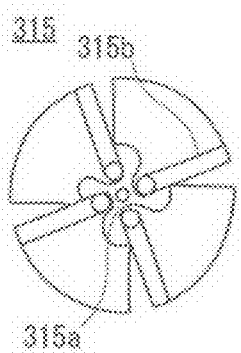

FIGS. 9(A) and 9(B) are views illustrating the accommodation unit 310 of the medical device according to Modification Example 2 (first example) of the embodiment. FIG. 9(A) is a view illustrating a cylinder 312 and an impeller 313 by using a cross section viewed from a side along the axial direction, and FIG. 9(B) is a view illustrating the impeller 313 viewed from the distal side toward the proximal side along the axial direction. FIGS. 10(A) and 10(B) are views illustrating the accommodation unit 310 of the medical device according to Modification Example 2 (second example) of the embodiment. FIG. 10(A) is a view illustrating the cylinder 312 and an impeller 314 by using a cross section viewed from a side along the axial direction, and FIG. 10(B) is a view illustrating the impeller 314 viewed from the distal side toward the proximal side along the axial direction. FIGS. 11(A) and 11(B) are views illustrating the accommodation unit 310 of the medical device according to Modification Example 2 (third example) of the embodiment. FIG. 11(A) is a view illustrating the cylinder 312 and an impeller 315 by using a cross section viewed from a side along the axial direction, and FIG. 11(B) is a view illustrating the impeller 315 viewed from the distal side toward the proximal side along the axial direction.

A simulation was performed in order to hydrodynamically analyze a flow of the fluid in the cylinder 312, based on data such as the shape of the cylinder or the impeller (for example, diameter of the lumen in the cylinder), a dynamic coefficient of viscosity of the fluid, pressure distribution, velocity vectors, and velocity distribution. As a result, through the following conditions, it was possible to obtain a preferable result (circulating flow G was formed from an aspiration section 312a to a discharge section 312c of the cylinder 312, thereby enabling a sufficient suction force to be generated).

In the accommodation unit 310 according to the first example to the third example, as illustrated in FIGS. 9(A) to 11(B), the cylinder 312 has the same configuration as the cylinder 112, and dimensions of each portion are specifically set in a hydrodynamic viewpoint. For example, considering that the cylinder 312 is introduced into a bent living body, the cylinder 312 is based on a premise that the entire length along the axial direction which can include the impeller-provided portion is, for example, 15 mm or shorter. In order to accommodate a sufficient amount of capturing targets in a lumen 312b, the cylinder 312 is based on a premise that the entire length along the axial direction of the impeller is set to, for example, 20% to 50% of the entire length along the axial direction of the cylinder 312.

The impellers 313, 314, and 315 have the same configuration as the impeller 113, and dimensions of each portion can be specifically set in a hydrodynamic viewpoint. The number of blade portions 313b, 314b, and 315b, which are rotatably formed in the impellers 313, 314, and 315 so as to move the fluid can be, for example, three to four.

Here, as illustrated in FIGS. 9(A) and 9(B), the radius of curvature in a cross section orthogonal to the axis of the blade portion 313b is, for example, 1.5 mm. As illustrated in FIGS. 10(A) and 10(B), the radius of curvature in a cross section orthogonal to the axis of the blade portion 314b is, for example, 3.0 mm. As illustrated in FIGS. 11(A) and 11(B), the radius of curvature in a cross section orthogonal to the axis of the blade portion 315b can be, for example, infinity (straight line).

In the above-described simulation, the radius of curvature in a cross section orthogonal to the axis of the blade portions is changed in accordance with a ratio of a region (length along the axial direction) in which the blade is exposed from the discharge section 312c. When the ratio of a region (length along the axial direction) in which the blade is exposed from the discharge section 312c is, for example, 40% or greater, the radius of curvature of the blade portion is set to, for example, 1.5 (more preferably 3.0) or greater. In accordance with an exemplary embodiment, when the ratio of a region (length along the axial direction) in which the blade is exposed from the discharge section 312c is smaller than, for example, 40%, the radius of curvature of the blade portion is set to, for example, 1.5 or smaller. The cross section orthogonal to the axis of the blade portion corresponds to, for example, 12% to 18% of the cross section orthogonal to the axis in the aspiration section 312a of the cylinder 312.

As described above, according to the medical device in Modification Example 2 of the embodiment, the following configurations provide an operation effect.

In the medical device, the length along the axial direction from a position of the aspiration section 312a of the cylinder 312 to the lumen 312b having the filter 111 arranged therein is formed to be, for example, 1 mm to 14 mm. According to the medical device having this configuration, the capturing target captured by the filter 111 can be sufficiently accommodated in the lumen 312b.

Furthermore, according to the medical device, the entire length of the cylinder 312 is, for example, 15 mm or shorter. At least a portion on the proximal side of the impeller 313 is arranged at a position facing the discharge section 312c in a region inside the lumen 312b. The length of the region facing the discharge section 312c is less than, for example, 40% of the entire length of the impeller 313. The radius of curvature in a cross section orthogonal to the axis of the blade portion 313b which is rotatably formed in the impeller 313 so as to move the fluid is formed to be, for example, 1.5 mm or shorter. According to the medical device having this configuration, it can be preferable to adopt this configuration, particularly when the cylinder 312 is introduced into the living body having a narrow site whose inner shape orthogonal to the axial direction shows several mm in unit so that the fluid which is aspirated from the aspiration section 312a and which moves radially outward due to centrifugal force generated by the rotation of the impeller 313 is discharged from the discharge section 312c. As a result, a flow of the fluid including the circulating flow G configured to partially have a flow of the fluid inside the lumen 312b from the aspiration section 312a toward the discharge section 312c is formed in the lumen 312b and around the cylinder 312. In this manner, in particular, the velocity of the fluid inside the lumen 312b which flows from the aspiration section 312a toward the discharge section 312c can be increased. That is, the medical device can sufficiently aspirate and capture the capturing target inside the living body having a narrow site whose inner shape orthogonal to the axial direction shows several mm in unit.

Furthermore, according to the medical device, the entire length of the cylinder 312 is, for example, 15 mm or shorter. At least a portion on the proximal side of the impeller 314 or 315 can be arranged at a position facing the discharge section 312c in a region inside the lumen 312b. The length of the region facing the discharge section 312c is, for example, equal to or greater than 40% of the entire length of the impeller 314 or 315. The radius of curvature in a cross section orthogonal to the axis of the blade portion 314b or 315b which is rotatably formed in the impeller 314 or 315 so as to move the fluid is formed to be in a range of, for example, 1.5 mm to infinity. According to the medical device having this configuration, it can be preferable to adopt this configuration, particularly when the cylinder 312 is introduced into the living body having a narrow site whose inner shape orthogonal to the axial direction shows several mm in unit so that the fluid which is aspirated from the aspiration section 312a and which moves radially outward due to centrifugal force generated by the rotation of the impeller 314 or 315 is discharged from the discharge section 312c. Furthermore, according to a configuration in which the entire length of the impeller 314 or 315 is shortened and a space for accommodating the capturing target is broadened, even when the length of the region facing the discharge section 312c of the impeller 314 or 315 is, for example, equal to or greater than 40% of the entire length of the impeller 314 or 315, a flow of the fluid including the circulating flow G configured to partially have a flow of the fluid inside the lumen 312b from the aspiration section 312a toward the discharge section 312c is formed in the lumen 312b and around the cylinder 312. In this manner, the velocity of the fluid inside the lumen 312b which flows from the aspiration section 312a toward the discharge section 312c can be increased. Therefore, a sufficient suction force around the aspiration section 312a can be generated. That is, the medical device can sufficiently aspirate and capture the capturing target inside the living body having a narrow site whose inner shape orthogonal to the axial direction shows several mm in unit.

A medical device according to Modification Example 3 of the embodiment will be described with reference to FIGS. 12(A) and 12(B). According to the medical device in Modification Example 3 of the embodiment, a configuration is different from the configuration of the medical device 100 according to Modification Example 2 (first example) of the above-described embodiment in that in order to increase a flow rate per unit time in the lumen 312b, control within a predetermined range is performed on a twisted degree of the blade portion in a direction from the upstream side toward the downstream side in the axial direction along the circumferential direction of the blade portion, and on an occupying ratio of a sectional area of a cross section orthogonal to the axis of the blade portion in a sectional area of a cross section orthogonal to the axis of the lumen of the cylinder. In Modification Example 3 according to the embodiment, the same reference numerals are given to the same configuration elements as those in the embodiment, and repeated description will be omitted.

A configuration of an accommodation unit 410 according to Modification Example 3 of the embodiment will be described with reference to FIGS. 12(A) and 12(B).

Figure 12A:
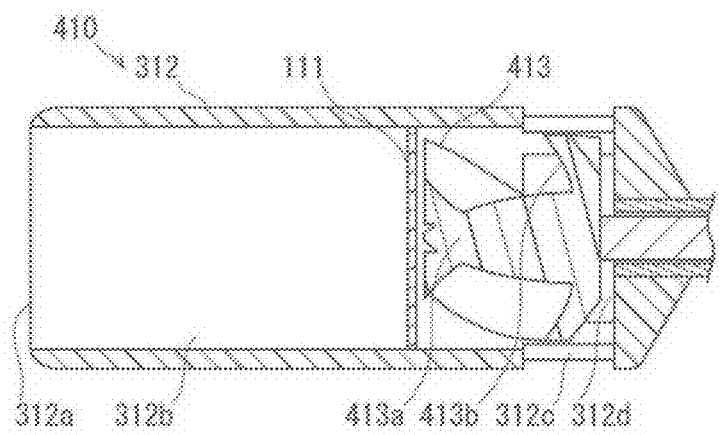
Figure 12B:
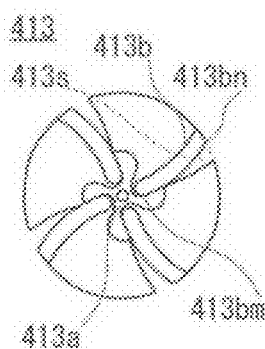

FIGS. 12(A) and 12(B) are views illustrating the accommodation unit 410 of the medical device according to Modification Example 3 of the embodiment. FIG. 12(A) is a view illustrating a cylinder 312 and an impeller 413 by using a cross section viewed from a side along the axial direction, and FIG. 12(B) is a view illustrating the impeller 413 viewed from the distal side toward the proximal side along the axial direction.

In the simulation of the flow of the fluid in the cylinder 312, based on the conditions according to the first example of Modification Example 2 of the embodiment, like the blade portion 413b of the impeller 413, control was performed on a twisted degree of the blade portion 413b in a direction from the upstream side toward the downstream side in the axial direction along the circumferential direction of the blade portion 413b, and on an occupying ratio of a sectional area of a cross section orthogonal to the axis of the blade portion 413b in a sectional area orthogonal to the axis of the lumen of the cylinder. As a result, a more preferable result can be obtained. That is, in the simulation, when the blade portion 413b is twisted in the direction from the upstream side toward the downstream side in the axial direction along the circumferential direction, or when control is performed on the occupying ratio of the sectional area of the cross section orthogonal to the axis of the blade portion 413b in the sectional area orthogonal to the axis of the lumen 312b of the cylinder 312, an increased flow rate per unit time in the lumen 312b can be obtained.

In the impeller 413, a twisted angle in the blade portion 413b is set to, for example, 70° in the direction from the upstream side toward the downstream side in the axial direction along the circumferential direction. In addition, the occupying ratio of the sectional area of the cross section orthogonal to the axis of the blade portion 413b in the sectional area of the cross section orthogonal to the axis of the lumen 312b of the cylinder 312 is set to, for example, 16.9%. In a case of this impeller 413, in the blade portions 413b adjacent to each other along the circumferential direction, a clearance 413s is visible in a region from an apex portion 413bm (near the center in the radial direction) to a bottom portion 413bn (outer peripheral edge along the radial direction) in the direction from the upstream side toward the downstream side in the axial direction. On the other hand, in the impeller 313 according to the first example of Modification Example 2 of the embodiment, a twisted angle along the circumferential direction of the respective blade portions 313b is set to, for example, 90°. In a case of this impeller 313, in the blade portions 313b adjacent to each other along the circumferential direction, the clearance is not visible in a region from an apex portion 313bm (near the center in the radial direction) to a bottom portion 313bn (outer peripheral edge along the radial direction) in the direction from the upstream side toward the downstream side in the axial direction.

The occupying ratio of the sectional area of the cross section orthogonal to the axis of the blade portion 413b in the sectional area of the cross section orthogonal to the axis of the lumen 312b, a size of the clearance 413s in the region from the apex portion 413bm (near the center in the radial direction) to the bottom portion 413bn (outer peripheral edge along the radial direction) in the direction from the upstream side toward the downstream side in the axial direction of the impeller 413, and a balance therebetween affect an amount per unit time of the fluid conveyed in the direction from the apex portion 413*bm* to the bottom portion 413*bn* by the rotation of the impeller 413. Therefore, the increased flow rate per unit time in the lumen 312*b* can be obtained by controlling these values.

In addition, in a case of the impeller 413, in the blade portions 413*b* adjacent to each other along the circumferential direction, the clearance 413*s* is visible in the region from the apex portion 413*bm* (near the center in the radial direction) to the bottom portion 413*bn* (outer peripheral edge along the radial direction) in the direction from the upstream side toward the downstream side in the axial direction. According to this configuration, when the impeller 413 is formed by performing a cutting process, a cutting tool can be inserted into the clearance between the blade portions 413*b*. Therefore, the impeller 413 can be processed so as to have structure in which the blade portions 413*b* are twisted in the direction from the apex portion 413*bm* toward the bottom portion 413*bn*. In addition, according to this configuration, when the impeller 413 is formed by means of injection molding, if multiple molds are used in combination, the impeller 413 can be processed so as to have a structure in which the blade portions 413*b* are twisted in the direction from the apex portion 413*bm* toward the bottom portion 413*bn*.

Incidentally, in a case of the impeller 313 according to the first example of Modification Example 2 of the embodiment, in the blade portions 313*b* adjacent to each other along the circumferential direction, the clearance is not visible in the region from the apex portion 313*bm* (near the center in the radial direction) to the bottom portion 313*bn* (outer peripheral edge along the radial direction) in the direction from the upstream side toward the downstream side in the axial direction. In this case, in order to process the impeller so as to have the structure in which the blade portions 313*b* are twisted in the direction from the apex portion 313*bm* toward the bottom portion 313*bn*, the impeller 313 itself is cut while being rotated, or a detachable mold is used while the impeller 313 itself is rotated. On the other hand, if the configuration of the impeller 413 according to Modification Example 3 of the embodiment is adopted, it is possible to uniformly control each shape or each weight of the multiple blade portions 313*b*.

In addition, in a case of the impeller 313 according to the first example of Modification Example 2 of the embodiment, a difference in the shape or the weight between the blade portions 313*b* affects a flow of the fluid which is formed by the rotation of the impeller 313, and a magnitude of a suction force which is generated as a result therefrom. Therefore, a configuration is adopted which allows easy processing as in the impeller 413 according to Modification Example 3 of the embodiment. In this manner, the difference in the shape or the weight between the blade portions 413*b* can be minimized. Accordingly, even at the time of production, the impeller 413 which provides a stable suction force or flow rate can be obtained.

As described above, according to the medical device in Modification Example 3 of the embodiment, the following configurations provide an operation effect.

According to the medical device, an inner diameter of the cylinder 312 is 10 mm or shorter. The number of blade portions 413*b* which are rotatably formed in the impeller 413 so as to move the fluid is, for example, three to five. A twisted angle of the blade portions 413*b* which are rotatably formed in the impeller 413 so as to move the fluid, in a direction from the upstream side toward the downstream side in the axial direction along the circumferential direction is, for example, 50° to 120°. An occupying ratio of the sectional area of the cross section orthogonal to the axis of the blade portion 413*b* in the sectional area of the cross section orthogonal to the axis of the lumen of the cylinder 312 is, for example, 12% to 18%. According to the medical device having this configuration, the fluid aspirated from the aspiration section 312*a* partially passes through the clearance 413*s* between the blade portions 413*b*. In this manner, the fluid can smoothly flow in the lumen 312*b*. Therefore, it is possible to increase a flow rate per unit time in the lumen 312*b*. That is, the medical device can vigorously aspirate and capture the capturing target in the lumen 312*b* inside the living body having a narrow site whose inner shape shows several mm in unit.

In addition, in the medical device, particularly according to conditions 1 to 3 below, the fluid aspirated from the aspiration section is caused to partially pass through the clearance between the blade portions. In this manner, the fluid can smoothly flow in the lumen. Therefore, it is possible to increase a flow rate per unit time in the lumen.

In accordance with an exemplary embodiment, in an exemplary embodiment, (condition 1), the entire length of the cylinder is, for example, 6.1 mm. The entire length of the impeller is, for example, 2.5 mm. A length of a region facing the discharge section on the proximal side of the impeller is, for example, 44% of the entire length of the impeller. The radius of curvature in a cross section orthogonal to the axis of blade portions which are rotatably formed in the impeller and which move the fluid is, for example, infinity. The number of the blade portions is, for example, four. A twisted angle of the blade portions in a direction from an upstream side toward a downstream side in the axial direction along a circumferential direction is, for example, 70°. An occupying ratio of a sectional area of a cross section orthogonal to the axis of the blade portions in a sectional area of a cross section orthogonal to the axis of the lumen of the cylinder is, for example, 16.9%.

In accordance with an exemplary embodiment, (condition 2), the entire length of the cylinder is, for example, 8.3 mm. The entire length of the impeller is, for example, 2.8 mm. A length of a region facing the discharge section on the proximal side of the impeller is, for example, 31.4% of the entire length of the impeller. The radius of curvature in a cross section orthogonal to the axis of blade portions which are rotatably formed in the impeller and which move the fluid is, for example, 1.5 mm. The number of the blade portions is, for example, three. A twisted angle of the blade portions in a direction from an upstream side toward a downstream side in the axial direction along a circumferential direction is, for example, 90°. An occupying ratio of a sectional area of a cross section orthogonal to the axis of the blade portions in a sectional area of a cross section orthogonal to the axis of the lumen of the cylinder is, for example, 13.1%.

In accordance with an exemplary embodiment, (condition 3), the entire length of the cylinder is, for example, 9 mm. The entire length of the impeller is, for example, 4 mm. A length of a region facing the discharge section on the proximal side of the impeller is, for example, 7.5% of the entire length of the impeller. The radius of curvature in a cross section orthogonal to the axis of blade portions which are rotatably formed in the impeller and which move the fluid is, for example, 1.5 mm. The number of the blade portions is, for example, four. A twisted angle of the blade portions in a direction from an upstream side toward a downstream side in the axial direction along a circumferential direction is, for example, 60°. An occupying ratio of a sectional area of a cross section orthogonal to the axis of the blade portions in a sectional area of a cross section orthogonal to the axis of the lumen of the cylinder is, for example, 15.2%.

Hitherto, the medical device according to the present disclosure has been described with reference to the multiple embodiment and modification examples. However, the present disclosure can be appropriately modified, based on content described in the scope of Claims.

For example, the medical device is not limited to a form in which the medical device is introduced into the urinary duct 630 so as to capture and remove the capturing target, and can be introduced into other sites inside the living body so as to capture and remove the capturing target. For example, the other sites inside the living body correspond to the renal pelvis and renal calyx 640.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
   a filter for capturing a capturing target present inside a living body;
   a cylinder that includes a lumen having the filter arranged in the cylinder, an aspiration section which is open on a distal side of the lumen, and a discharge section which is open on a side surface on a proximal side of the lumen, the discharge section being configured to discharge a fluid passing through the filter into the living body, and thereby allowing a flow of the fluid in a circumferential direction of the cylinder;
   an impeller that is arranged on a proximal side of the filter in the lumen, and that causes the lumen to aspirate the capturing target together with the fluid by causing the fluid to flow from the aspiration section toward the discharge section inside the living body, wherein at least a portion of the impeller is arranged between a distal end and a proximal end of the discharge section along an axial direction of the cylinder; and
   the cylinder including a proximal wall on a most proximal side of the cylinder, and wherein the flow of a part of the fluid is through the impeller to the proximal wall and radially outward from the discharge section located on the side surface of the cylinder into the living body to the aspiration section, and wherein the at least a portion of the proximal portion of the impeller is arranged at a position facing the discharge section in a region inside the lumen.

2. The medical device according to claim 1, wherein the proximal wall is proximal of the discharge section, and the proximal wall is bent into a concave shape.

3. The medical device according to claim 2, wherein the proximal wall is continuously bent including the discharge section.

4. The medical device according to claim 1, wherein a length along the axial direction from a position of the aspiration section of the cylinder to the lumen having the filter 1 mm to 14 mm.

5. The medical device according to claim 1, wherein an entire length of the cylinder is 15 mm or shorter;
   wherein a length of the region facing the discharge section is shorter than 40% of an entire length of the impeller; and
   wherein a radius of curvature in a cross section orthogonal to an axis of a blade portion which is rotatably formed in the impeller to move the fluid is 1.5 mm or shorter.

6. The medical device according to claim 1, wherein an entire length of the cylinder is 15 mm or shorter;
   wherein a length of the region facing the discharge section is equal to or greater than 40% of an entire length of the impeller; and
   wherein a radius of curvature in a cross section orthogonal to an axis of a blade portion which is rotatably formed in the impeller to move the fluid is 1.5 mm to infinity.

7. The medical device according to claim 1, wherein an inner diameter of the cylinder is 10 mm or shorter;
   wherein a number of blade portions which are rotatably formed in the impeller to move the fluid is three to five;
   wherein a twisted angle of the blade portions which are rotatably formed in the impeller to move the fluid, in a direction from an upstream side toward a downstream side in the axial direction along a circumferential direction is 50° to 120°; and
   wherein an occupying ratio of a sectional area of a cross section orthogonal to an axis of the blade portion in a sectional area of a cross section orthogonal to an axis of the lumen of the cylinder is 12% to 18%.

8. The medical device according to claim 1,
   wherein an entire length of the cylinder is 6.1 mm;
   wherein an entire length of the impeller is 2.5 mm;
   wherein a length of a region facing the discharge section of the impeller is 44% of the entire length of the impeller;
   wherein a radius of curvature in a cross section orthogonal to an axis of blade portions which are rotatably formed in the impeller to move the fluid is infinity;
   wherein a number of the blade portions is four;
   wherein a twisted angle of the blade portions in a direction from an upstream side toward a downstream side in the axial direction along a circumferential direction is 70°; and
   wherein an occupying ratio of a sectional area of a cross section orthogonal to the axis of the blade portions in a sectional area of a cross section orthogonal to an axis of the lumen of the cylinder is 16.9%.

9. The medical device according to claim 1,
   wherein an entire length of the cylinder is 8.3 mm;
   wherein an entire length of the impeller is 2.8 mm;
   wherein a length of a region facing the discharge section of the impeller is 31.4% of the entire length of the impeller;
   wherein a radius of curvature in a cross section orthogonal to an axis of blade portions which are rotatably formed in the impeller to move the fluid is 1.5 mm;
   wherein a number of the blade portions is three;
   wherein a twisted angle of the blade portions in a direction from an upstream side toward a downstream side in the axial direction along a circumferential direction is 90°; and wherein an occupying ratio of a sectional area of a cross section orthogonal to the axis of the blade portions in a sectional area of a cross section orthogonal to an axis of the lumen of the cylinder is 13.1%.

10. The medical device according to claim 1,
wherein an entire length of the cylinder is 9 mm;
wherein an entire length of the impeller is 4 mm;
wherein a length of a region facing the discharge section of the impeller is 7.5% of the entire length of the impeller;
wherein a radius of curvature in a cross section orthogonal to an axis of blade portions which are rotatably formed in the impeller to move the fluid is 1.5 mm;
wherein a number of the blade portions is four;
wherein a twisted angle of the blade portions in a direction from an upstream side toward a downstream side in the axial direction along a circumferential direction is 60°; and
wherein an occupying ratio of a sectional area of a cross section orthogonal to the axis of the blade portions in a sectional area of a cross section orthogonal to an axis of the lumen of the cylinder is 15.2%.

11. A method for capturing a target present inside a living body, the method comprising:
inserting a medical device comprising a filter for capturing a capturing target, a cylinder that includes a lumen having the filter arranged in the cylinder, an aspiration section which is open on a distal side of the lumen, a discharge section which is open on a side surface on a proximal side of the lumen, and an impeller that is arranged on a proximal side from the filter in the lumen, wherein at least a portion of the impeller is arranged between a distal end and a proximal end of the discharge section along an axial direction of the cylinder, the discharge section being configured to discharge a fluid passing through the filter into the living body, and thereby allowing a flow of the fluid in a circumferential direction of the cylinder, the cylinder including a proximal wall on a most proximal side of the cylinder, and wherein the flow of a part of the fluid is through the impeller to the proximal wall and radially outward from the discharge section located on the side surface of the cylinder into the living body to the aspiration section, and wherein the at least a portion of the proximal portion of the impeller is arranged at a position facing the discharge section in a region inside the lumen; and
aspirating the capturing target with the lumen and the fluid by flowing the fluid from the aspiration section toward the discharge section inside the living body.

12. The method according to claim 11, comprising:
forming the cylinder so that the proximal wall which is further separated from the aspiration section and proximally of the discharge section, and wherein the proximal wall is bent into a concave shape.

13. The method according to claim 12, comprising:
forming the proximal wall to be continuously bent including the discharge section.

14. The method according to claim 11, comprising:
forming a length along the axial direction from a position of the aspiration section of the cylinder up to the lumen having the filter arranged in the cylinder to be 1 mm to 14 mm.

15. The method according to claim 11, comprising:
wherein an entire length of the cylinder is 15 mm or shorter;
wherein a length of the region facing the discharge section is shorter than 40% of an entire length of the impeller; and
wherein a radius of curvature in a cross section orthogonal to an axis of a blade portion which is rotatably formed in the impeller to move the fluid is 1.5 mm or shorter.

16. The method according to claim 11, comprising:
wherein an entire length of the cylinder is 15 mm or shorter;
wherein a length of the region facing the discharge section is equal to or greater than 40% of an entire length of the impeller; and
wherein a radius of curvature in a cross section orthogonal to an axis of a blade portion which is rotatably formed in the impeller to move the fluid is 1.5 mm to infinity.

17. The method according to claim 11,
wherein an inner diameter of the cylinder is 10 mm or shorter;
wherein a number of blade portions which are rotatably formed in the impeller to move the fluid is three to five;
wherein a twisted angle of the blade portions which are rotatably formed in the impeller to move the fluid, in a direction from an upstream side toward a downstream side in the axial direction along a circumferential direction is 50° to 120°; and
wherein an occupying ratio of a sectional area of a cross section orthogonal to an axis of the blade portion in a sectional area of a cross section orthogonal to an axis of the lumen of the cylinder is 12% to 18%.

18. A medical device comprising:
a filter for capturing a capturing target present inside a living body;
a cylinder that includes a lumen having the filter arranged in the cylinder, an aspiration section which is open on a distal side of the lumen, and a discharge section which is open on a side surface on a proximal side of the lumen, the discharge section being configured to discharge a fluid passing through the filter into the living body, and thereby allowing a flow of the fluid in a circumferential direction of the cylinder;
an impeller that is arranged on a proximal side of the filter in the lumen, and that causes the lumen to aspirate the capturing target together with the fluid by causing the fluid to flow from the aspiration section toward the discharge section inside the living body, wherein at least a portion of the impeller is arranged between a distal end and a proximal end of the discharge section along an axial direction of the cylinder; and
the cylinder including a proximal portion on a most proximal side of the cylinder, and wherein the proximal portion has a support hole configured to support an axle portion of the impeller, and wherein the flow of a part of the fluid is through the impeller to the proximal portion and radially outward from the discharge section located on the side surface of the cylinder into the living body to the aspiration section, and wherein the at least a portion of the proximal portion of the impeller is arranged at a position facing the discharge section in a region inside the lumen.

19. The medical device according to claim 18,
wherein the proximal portion is proximal of the discharge section, and the proximal portion is bent into a concave shape.

20. The medical device according to claim 19, wherein the proximal portion is continuously bent including the discharge section.

* * * * *